United States Patent
Hodges et al.

(10) Patent No.: US 11,355,230 B1
(45) Date of Patent: Jun. 7, 2022

(54) SYSTEM AND METHOD OF SELECTIVELY SHOWING TRACTOGRAPHY IN AREAS CONTAINING FREE WATER

(71) Applicant: SYNAPTIVE MEDICAL INC., Toronto (CA)

(72) Inventors: Wesley Bryan Hodges, Toronto (CA); Alicia McNeely, Toronto (CA); Sebastian Koga, Toronto (CA); Tim Hayes, Toronto (CA); Hayk Adamyan, Burlington (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 0 days.

(21) Appl. No.: 17/502,278

(22) Filed: Oct. 15, 2021

Related U.S. Application Data (60) Provisional application No. 63/161,585, filed on Mar. 16, 2021, provisional application No. 63/144,639, filed on Feb. 2, 2021.

(51) Int. Cl.
| | | |
|---|---|---|
| *G06F 3/04847* | (2022.01) | |
| *G16H 30/20* | (2018.01) | |
| *G16H 20/40* | (2018.01) | |
| *G06F 3/04845* | (2022.01) | |
| *A61B 5/055* | (2006.01) | |

(52) U.S. Cl.
CPC ............ *G16H 30/20* (2018.01); *A61B 5/055* (2013.01); *G06F 3/04845* (2013.01); *G06F 3/04847* (2013.01); *G16H 20/40* (2018.01)

(58) Field of Classification Search
None
See application file for complete search history.

(56) References Cited

U.S. PATENT DOCUMENTS

| | | | |
|---|---|---|---|
| 2010/0312096 A1* | 12/2010 | Guttman | A61B 34/25 600/411 |
| 2015/0310652 A1* | 10/2015 | Dobson | G06F 3/04845 345/629 |
| 2017/0345149 A1* | 11/2017 | Warntjes | A61B 5/0042 |
| 2020/0200899 A1* | 6/2020 | Aase | G01S 7/52053 |

OTHER PUBLICATIONS

"Analyzing the effects of free water modeling by deep learning on diffusion MRI structural connectivity estimates in glioma patients" Published on Sep. 25, 2020, Authors: Weninger et al. https://journals.plos.org/plosone/article?id=10.1371/journal.pone.0239475.*

(Continued)

*Primary Examiner* — Rinna Yi
(74) *Attorney, Agent, or Firm* — Perry + Currier Inc.

(57) ABSTRACT

A system and method of tractography labelling in the presence of a brain lesion. According to the disclosure, a composition of free water correction (FWC) tractography and non-FWC tractography sets into a single tractography set with a 'degree of free water' value assigned to each tract and/or fragment of tract geometry. A slider graphical user interface is introduced to dynamically adjust the free water threshold value that controls what tracts and/or fragments of tract geometry get shown. For example, only tracts or fragments of tract geometry with a degree of free water below the threshold are shown while the rest are hidden.

2 Claims, 7 Drawing Sheets

(56) References Cited

OTHER PUBLICATIONS

"Free water elimination and mapping from diffusion MRI" Published on Jul. 21, 2009, Authors: Pasternak et al. https://onlinelibrary.wiley.com/doi/10.1002/mrm.22055.*

"Deep Learning with Synthetic Diffusion MRI Data for Free-Water Elimination in Glioblastoma Cases" Published on Sep. 13, 2018, Authors: Molina-Romero et al. https://link.springer.com/chapter/10.1007/978-3-030-00931-1_12.*

Parker, D., et al. "Freewater estimatoR using iNtErpolated iniTialization (FERNET): Characterizing peritumoral edema using clinically feasible diffusion MRI data." Plos one 15.5 (2020): e0233645-e0233645.

Henderson Jr, F., et al. "Enhanced Fiber Tractography Using Edema Correction: Application and Evaluation in High-Grade Gliomas." Neurosurgery (2021).

* cited by examiner

SYSTEM AND METHOD OF SELECTIVELY SHOWING TRACTOGRAPHY IN AREAS CONTAINING FREE WATER

CROSS REFERENCE TO RELATED APPLICATIONS

This application claims priority from United States Patent Application Nos. 63/144,639 filed Feb. 2, 2021 and 63/161,585 filed Mar. 16, 2021, the contents of which are incorporated herein by reference.

BACKGROUND

The field of the invention is systems and methods for surgical planning, in particular, a system and method of selectively displaying free water in tractography.

In neuroscience, tractography is a 3D modeling technique used for subjective surgical decision making by visually representing nerve fibers (tracts) using data collected by diffusion magnetic resonance imaging (MRI). The results of tractography are presented in two- and three-dimensional images referred to as tractograms, which surgeons use to choose a surgical trajectory having a path of least destruction to white matter (i.e. matter containing nerve tracts found in the deeper tissues of the brain (subcortical), which are surrounded by a white myelin sheath or covering). Advanced tractography algorithms can produce 90% of nerve tracts, but can be confounded by the presence of edema (swelling), which is extracellular fluid that can move in any direction (i.e., otherwise known as 'free water'). This isotropic free water hides anisotropic water (i.e., tracts) during magnetic resonance imaging (MRI).

Methods for subtracting out the free water from an MRI signal so as not to occlude a desired anisotropic tract, are known as free water correction (FWC) algorithms (for example, see Fraser Henderson Jr, MD, Drew Parker, BSc, Anupa A. Vijayakumari, PhD, Mark Elliott, PhD, Timothy Lucas, MD, PhD, Michael L. McGarvey, MD, Lauren Karpf, BSc, Lisa Desiderio, RT, Jessica Harsch, BSc, Scott Levy, BSc, Eileen Maloney-Wilensky, NP, Ronald L. Wolf, MD, PhD, Wesley B. Hodges, BASc, Steven Brem, MD, Ragini Verma, PhD, *Enhanced Fiber Tractography Using Edema Correction: Application and Evaluation in High-Grade Gliomas*, NEUROSURGERY VOLUME 0|NUMBER 0|2021, hereinafter Henderson, et al.].

Since different pathologies, such as glioblastomas and brain metastases, present free water differently, MRI images of tracts in the presence of different pathologies may be subjected to different degrees of occlusion based on free water content.

Thus a problem exists in tractography when displaying non-pathological free water areas and different pathologies.

SUMMARY

A system and method are set forth for selectively displaying free water in tractography. In one aspect, free water data and post-processed tract data are combined into a single tractography set with a 'degree of free water' value assigned to each tract and/or fragment of tract geometry, such as tract segments and/or points. A slider graphical user interface is provided to dynamically adjust the free water threshold value that controls which tracts and/or fragments of tract geometry are displayed. For example, only tracts or fragments of tract geometry with a degree of free water below the threshold value may be displayed while others are hidden.

According to an aspect, a method is provided for selectively displaying free water in tractography, comprising: applying a free water correction algorithm to an MRI image and assigning degree of free water values, which can be actual estimated percentages of free water or other metrics related to free water content, to each tract and/or fragment of tract geometry in the MRI image; comparing the degree of free water values to a threshold indicated by a slider interface; and refreshing the MRI image so that only those tracts and/or fragments of tract geometry having degree of free water values less than or equal to the threshold are displayed, while others are hidden According to another aspect, a system is provided for selectively displaying free water in tractography, comprising: an MRI system for generating an MRI image, the MRI system including a data processing system for applying a free water correction algorithm to the MRI image and assigning degree of free water values to each tract and/or fragment of tract geometry in the MRI image; a graphical user interface having a first area for displaying the MRI image, and a second area with user interface elements for controlling aspects of the MRI image displayed in the first area; a free water correction slider interface in the second area for indicating a threshold of free water, in response to which the MRI system compares the degree of free water values to the threshold indicated by the slider interface and refreshes the MRI image so that only those tracts and/or fragments of tract geometry having degree of free water values less than or equal to the threshold are displayed, while others are hidden.

DETAILED DESCRIPTION

As discussed briefly above, by dynamically adjusting the degree of free water correction applied during tractography tracts and/or fragments of tract geometry may be selectively displayed, without the need to reprocess/regenerate a tract set. As set forth below, by assigning to each tract and/or fragment of tract geometry a normalized value indicating its degree of free water, and dynamically adjusting a free water threshold value tracts and/or fragments of tract geometry may be selectively displayed for different pathologies and to avoid false positives due to overcorrecting in certain non-pathological free water areas (e.g., the ventricles). Furthermore, a simple slider graphical user interface may be used to vary the free water threshold value. For example, setting the slider at, say, 80%, only tracts and/or fragments of tract geometry that appear in areas with very high degrees of free water will be displayed (i.e. up to 80%, such as in the ventricles).

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor. A "module" can be considered as a processor executing computer-readable code.

A processor as described herein can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, or microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. In some embodiments, a processor can be a graphics processing unit (GPU). The parallel processing capabilities of GPUs can reduce the amount of time for training and using neural networks (and other machine learning models) compared to central processing units (CPUs). In some embodiments, a processor can be an ASIC including dedicated machine learning circuitry custom-build for one or both of model training and model inference.

The disclosed or illustrated tasks can be distributed across multiple processors or computing devices of a computer system, including computing devices that are geographically distributed.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

Figure 1:
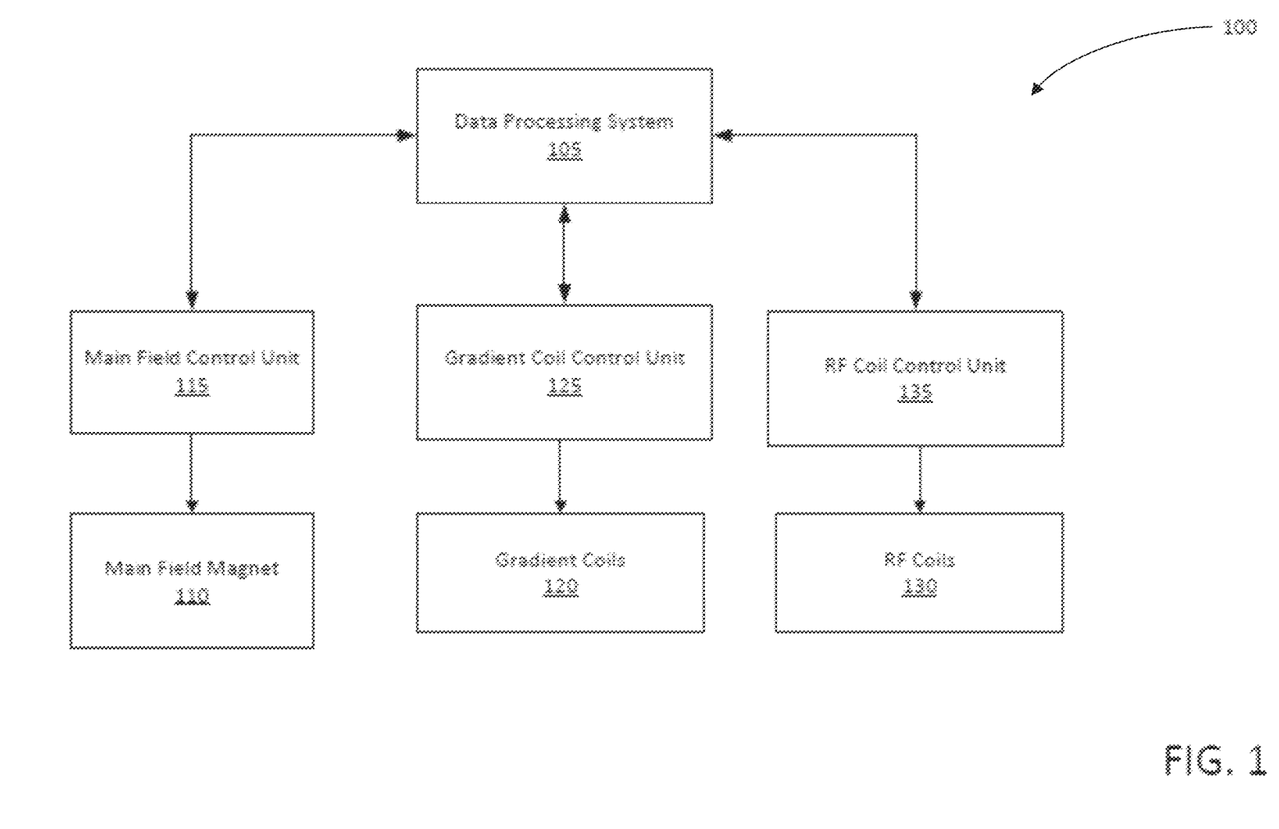
FIG. 1 is a block diagram of functional subsystems of an MRI system in accordance with an implementation.

Referring to FIG. 1, a block diagram of a magnetic resonance imaging (MRI) system, in accordance with an exemplary implementation, is shown at 100. The example implementation of MRI system indicated at 100 is for illustrative purposes only, and variations including additional, fewer and/or varied components are possible. MRI is an imaging modality which is primarily used to construct pictures of nuclear magnetic resonance (NMR) signals from hydrogen atoms in an object. In medical MRI, typical signals of interest are NMR signals from water and fat, the major hydrogen containing components of tissues.

As shown in FIG. 1, the MRI system 100 comprises a data processing system 105. The data processing system 105 generally comprises one or more output devices such as a display, one or more input devices such as a keyboard and a mouse as well as one or more processors connected to a memory having volatile and persistent components. The data processing system 105 further comprises an interface adapted for communication and data exchange with the hardware components of MRI system 100 used for performing a scan.

Continuing with FIG. 1, example MRI system 100 also includes a main field magnet 110. The main field magnet 110 can be implemented as a permanent, superconducting or a resistive magnet, for example. Other magnet types, including hybrid magnets suitable for use in MRI system 100 will now occur to a person of skill and are contemplated. Main field magnet 110 is operable to produce a substantially uniform magnetic field B0 having a direction along an axis. The magnetic field B0 is used to create an imaging volume within which desired atomic nuclei, such as the protons in Hydrogen within water and fat, of an object are magnetically aligned in preparation for a scan. In some implementations, as in this example implementation, a main field control unit 115 in communication with data processing system 105 can be used for controlling the operation of main field magnet 110.

MRI system 100 further includes gradient coils 120 used for encoding spatial information in the main magnetic field B0 along, for example, three perpendicular axis. The size and configuration of the gradient coils 120 can be such that they produce a controlled and uniform linear gradient. For example, three paired orthogonal current-carrying gradient coils 120 located within the main field magnet 110 can be designed to produce desired linear gradient magnetic fields. The magnetic fields produced by the gradient coils 120, in combination and/or sequentially, can be superimposed on the main magnetic field B0 such that selective spatial excitation of objects within the imaging volume can occur. In addition to allowing spatial excitation, the gradient coils 120 can attach spatially specific frequency and phase information to the atomic nuclei, allowing the resultant MR signal to be reconstructed into a useful image. A gradient coil control unit 125 in communication with data processing system 100 is used to control the operation of gradient coils 120.

The MRI system 100 further comprises radio frequency (RF) coils 130. The RF coils 130 are used to establish a magnetic field B1 to excite the atomic nuclei or "spins". The RF coils 130 can also detect signals emitted from the "relaxing" spins within the object being imaged. Accordingly, the RF coils 130 can be in the form of separate transmit and receive coils or a combined transmit and receive coil with a switching mechanism for switching between transmit and receive modes.

The RF coils 130 can be implemented as surface coils, which are typically receive only coils and/or volume coils which can be receive and transmit coils. RF coils 130 can be integrated in the main field magnet 110 bore. Alternatively, RF coils 130 can be implemented in closer proximity to the object to be scanned, such as a head, and can take a shape that approximates the shape of the object, such as a close-fitting helmet. An RF coil control unit 135 in communication with data processing system 100 is used to control the operation of the RF coils 130.

To create an image, MRI system 100 detects the presence of atomic nuclei containing spin angular momentum in an object, such as those of hydrogen protons in water or fat found in tissues, by subjecting the object to a large magnetic field. In this example implementation the main magnetic field is denoted as B0 and the atomic nuclei containing spin angular momentum will be Hydrogen protons or simply protons. Magnetic field B0 partially polarizes the Hydrogen protons in the object placed in the imaging volume of the main magnet 110. The protons are then excited with appropriately tuned RF radiation, in this example magnetic field B1. Finally, weak RF radiation signal from the excited protons is detected as they "relax" from the magnetic interaction. The frequency of the detected signal is proportional to the magnetic field to which they are subjected. Cross-section of the object from which to obtain signals can be selected by producing a magnetic field gradient across the object so that magnetic field values of B0 can be varied along various locations in the object. Given that the signal frequency is proportional to the varied magnetic field created, the variations allow assigning a particular signal frequency and phase to a location in the object. Accordingly, sufficient information can be found in the obtained signals to construct a map of the object in terms of proton presence, which is the basis of an MRI image. For example, since proton density varies with the type of tissue, tissue variations can be mapped as image contrast variations after the obtained signals are processed.

To obtain images from the MRI system 100 in the manner described above, one or more sets of RF pulses and gradient waveforms (collectively called "pulse sequences") are selected at the data processing system 105. The data processing system 105 passes the selected pulse sequence information to the RF control unit 135 and the gradient control unit 125, which collectively generate the associated waveforms and timings for providing a sequence of pulses to perform a scan.

For tractography, data processing system 105 can include known processes for diffusion tensor imaging (DTI) to map white matter tractography in the brain by measuring the apparent diffusion coefficient at each voxel in the image, and after multilinear regression across multiple images, reconstructing the whole diffusion tensor resulting in MRI images with each anisotropy linked to an orientation of the predominant axis (predominant direction of the diffusion). Post-processing programs may then be used to extract this directional information and by introducing a color code, show how the fibers are oriented in a 3D coordinate system (known as an "anisotropic map") where, for example, red indicates directions in the X axis: right to left or left to right, green indicates directions in the Y axis: posterior to anterior or from anterior to posterior, and blue indicates directions in the Z axis: foot-to-head direction or vice versa.

Figure 2:
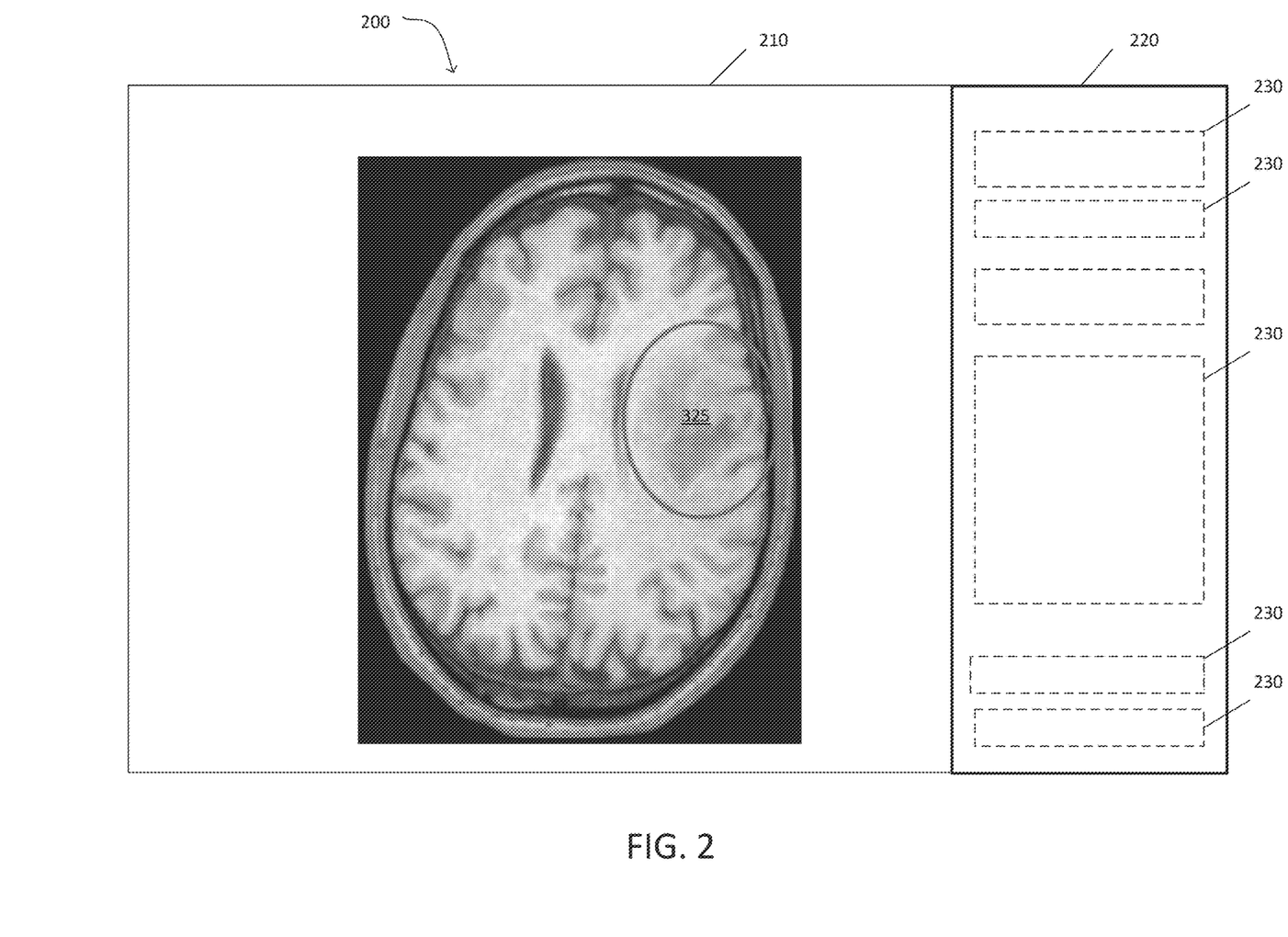
FIG. 2 is a diagram illustrating an MRI graphical user interface for tractography having a free water correction (FWC) slider interface, according to an embodiment.

FIG. 2 is a diagram illustrating an MRI graphical user interface 200 for tractography having a first area 210 for displaying an image, acquired for example using the MRI system 100 of FIG. 1, and a second area 220 with user interface elements 230 for controlling aspects of the image displayed in area 210, such as selections such as checkboxes (not shown) to select "intersecting tracts only", or for filtering data, such as hiding certain fibers (e.g. blue marked motor fibers that run head-to-foot, red marked fibers running left-to-right for carrying information to different hemispheres of the brain, or green marked projection fibers connecting lower and higher order processing regions of the brain).

Figure 3:
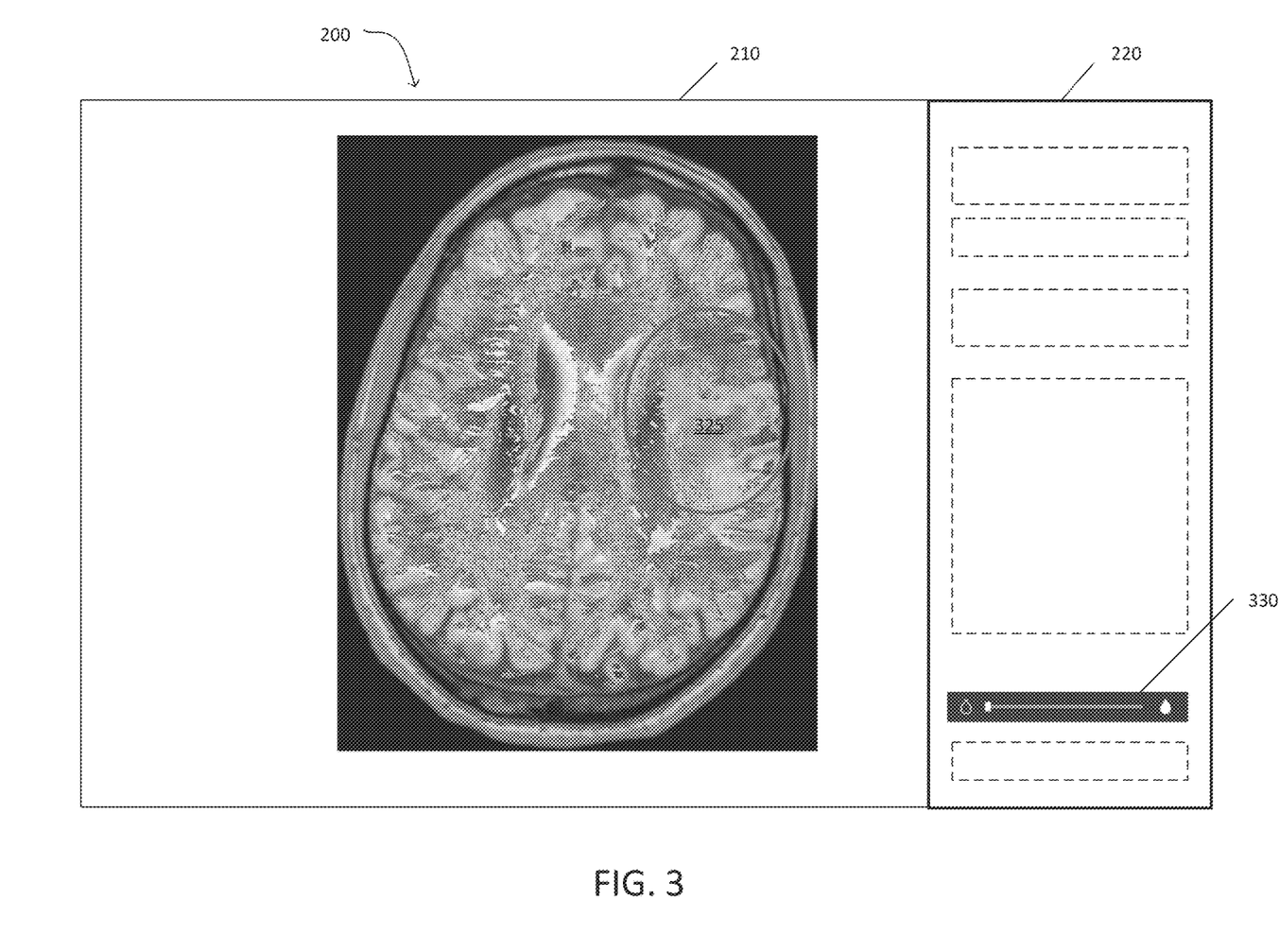
FIG. 3 is a diagram illustrating the MRI graphical user interface of FIG. 1 with the free water correction (FWC) slider interface user interface at 0%.

In FIG. 3 the image of FIG. 2 is enhanced to include a tractography set showing bundles of tracts, where 325 denotes an area of increased free water due, for example, to an edema. As discussed above, whereas tractography algorithms can produce 90% of nerve tracts, such algorithms can be confounded by areas of increased free water, such as at 325, which hide anisotropic water (i.e., tracts) during magnetic resonance imaging (MRI).

Figure 4:
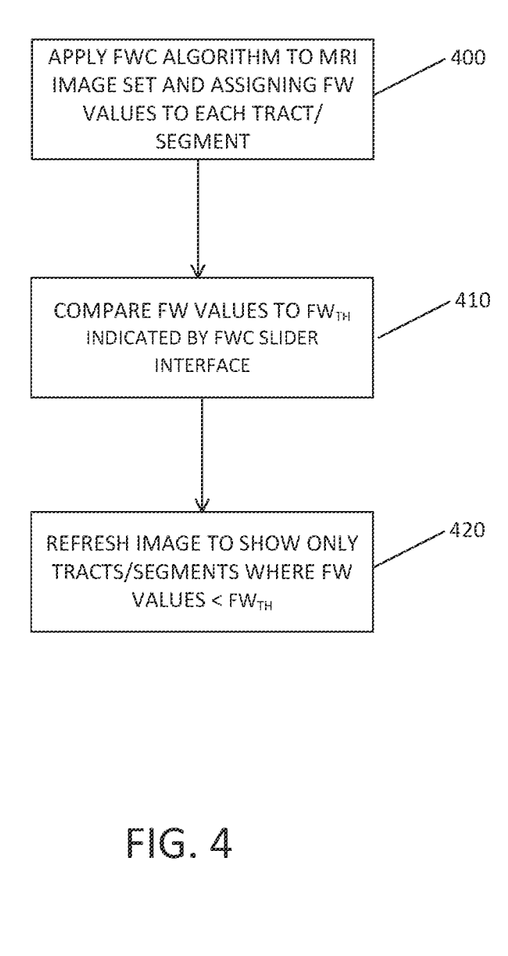
FIG. 4 is a diagram illustrating the MRI graphical user interface of FIG. 1 with the free water correction (FWC) slider interface user interface at 50%.

Therefore, according to an aspect of this specification, the second area 220 of user interface elements 230 includes a free water correction (FWC) slider interface 330 to control which tracts and/or fragments of tract geometry are displayed based on the degree of free water in the image according to a method, for example as shown in FIG. 4.

FIG. 4 is a flowchart showing a method for selectively displaying free water in the first area 200, using the FWC slider interface 330. At 400, an FWC algorithm is applied to the MRI image set resulting in a tractography set with a 'degree of free water' value (FW value) assigned to each tract and/or fragment of tract geometry. As discussed above, the FWC algorithm may be any of a number of known algorithms, such as described in Henderson, et al. At 410, the FW values assigned to all tracts and/or and fragments of tract geometry are compared to a user selected threshold ($FW_{TH}$) indicated by the FWC slider interface 330. At 420, the image in area 200 is refreshed so that only those tracts and/or fragments of tract geometry having FW values less than or equal to $FW_{TH}$ are displayed, while others are hidden.

In FIG. 3 the slider interface 330 is set at 0% such that the image in area 200 shows only tracts/segments where the FW value is less than or equal to a threshold $FW_{TH}$ of zero (i.e. no free water correction). Thus, the MRI image shown in area 200 includes gaps in tractography due to signal washout in the area 325 of increased free water.

Figure 5:
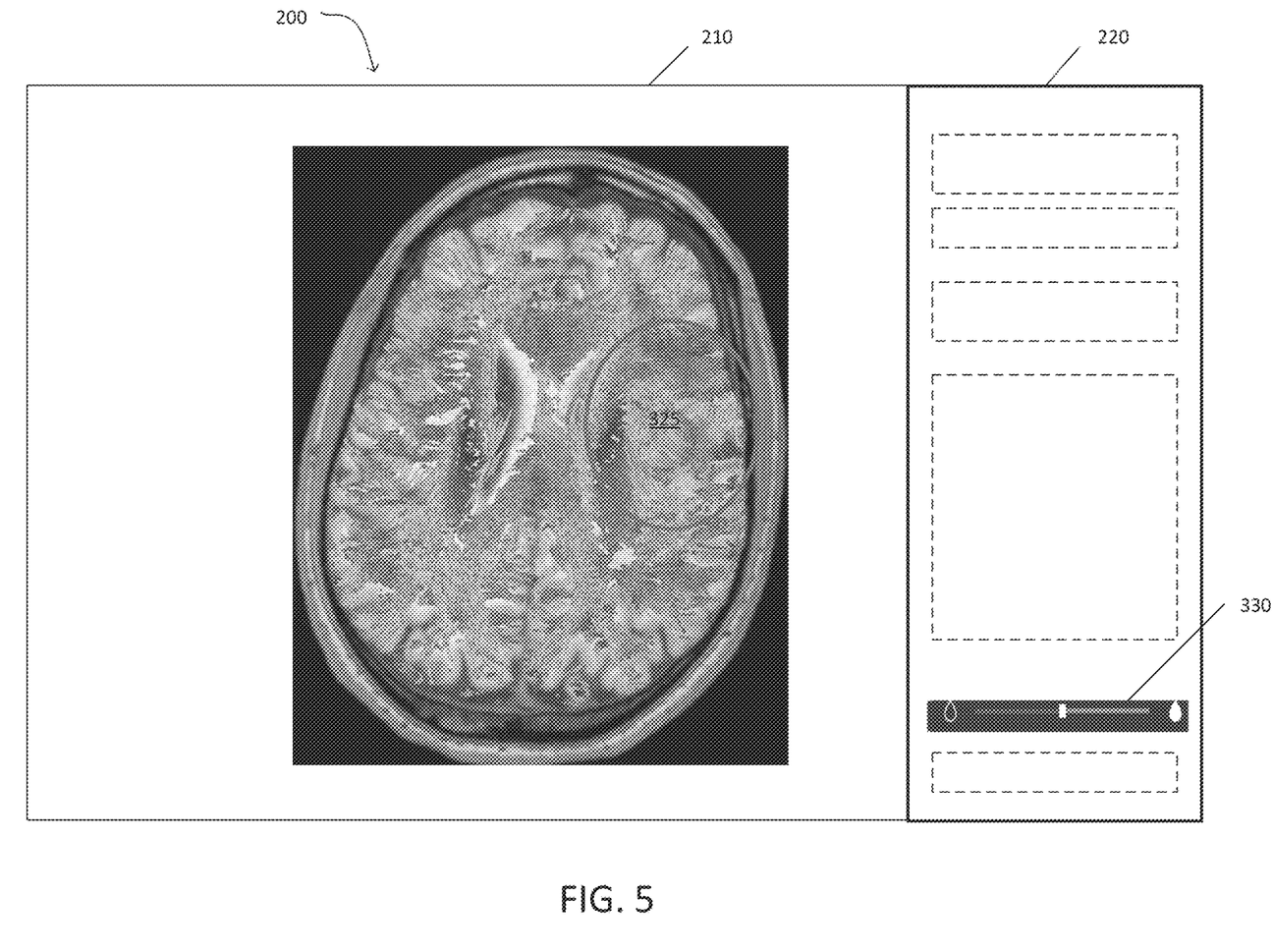
FIG. 5 is a diagram illustrating the MRI graphical user interface of FIG. 1 with the free water correction (FWC) slider interface user interface at 100%.

In FIG. 5, the slider interface 330 is set at 50% such that the MRI image shown in area 200 include additional tracts that are 'barely' hidden by free water (i.e. tracts where the assigned FW values <FWTH=50%). It should be noted that setting the slider interface 330 at 50% may or may not actually map to 50% free water value since, in embodiments, the slider value may be remapped via a look-up table to ensure uniform visibility control over the entire range of the slider. This avoids problems arising when a large portion of the FW values fall into a very narrow range such that an incremental movement of the slider would hide too many tracts/segments/points at one position on the slider, and remove too little (or none) at another position on the slider.

Figure 6:
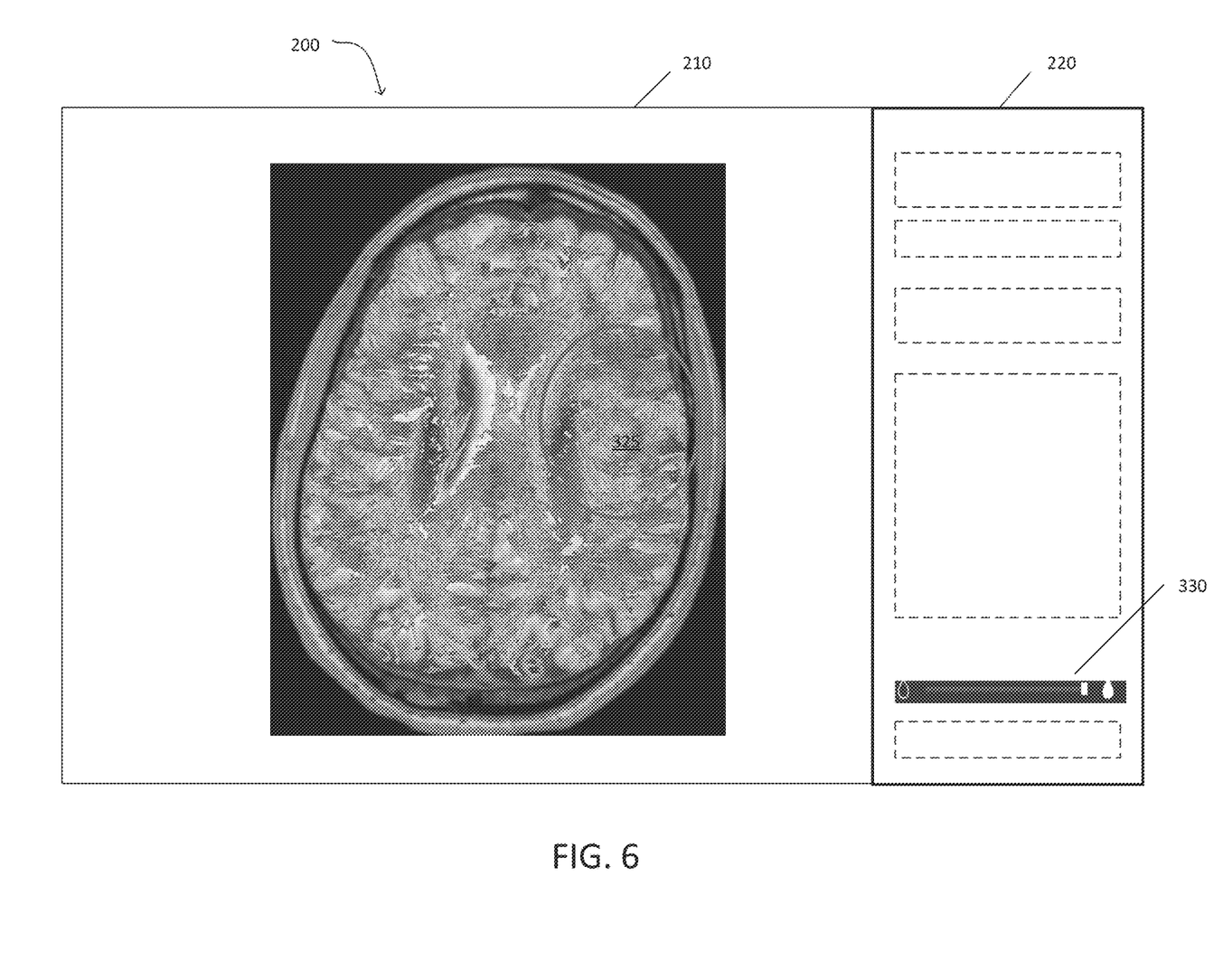
FIG. 6 is a flowchart showing steps in a method for generating the MRI graphical user interface for tractography of FIG. 1, according to an embodiment.

In FIG. 6, the slider interface 330 is set at 100% for aggressive free water correction, such that the MRI image shown in area 200 includes all tracts where the assigned FW values <$FW_{TH}$=100% (i.e. full free water corrected tractography), including tracts that were significantly occluded by free water.

Figure 7:
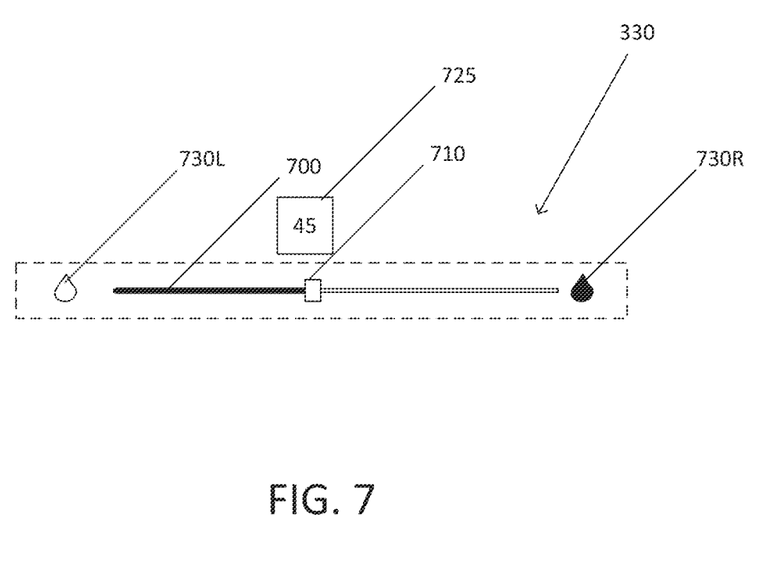
FIG. 7 shows additional details of the free water correction (FWC) slider interface user interface, according to an embodiment.

FIG. 7 shows additional details of the slider interface 330, according to an embodiment, including a track 700 showing the range that is available for a user to select from. From left-to-right, the smallest threshold value appears on the far left end of the track 700 and the largest value is on the far right. Thumb 710 is a position indicator that can be moved along the track 710. Optionally, a value label 725 can be included over the thumb 720 to display the value of its position as a numeral (e.g. "45" for $FW_{TH}$=45%). As a further option, tick marks may be included along the track 700 representing predetermined values that the user can move the slider to (e.g. 0%, 10%, 20% . . . 100%). Icons 730L and 730R are provided on both ends of the track 700 to provide a visual representation of a range of threshold values with icon 730L indicating no free water correction and icon 730R indicating full free water correction.

While the foregoing written description of the system enables one of ordinary skill to make and use what is considered presently to be the best mode thereof, those of ordinary skill will understand and appreciate the existence of variations, combinations, and equivalents of the specific embodiment, method, and examples herein. For example, whereas the exemplary FWC slider interface 330 described herein shows the smallest threshold value appearing on the far left end of the track 700 and the largest value on the far right, the FWC slider interface 330 can be implemented in the opposite direction, from right-to-left, wherein the left position shows the full water corrected set and right position shows the uncorrected set. The system should therefore not be limited by the above described embodiment, method, and examples, but by all embodiments and methods within the scope and spirit of the system. Thus, the present disclosure is not intended to be limited to the implementations shown herein but is to be accorded the widest scope consistent with the principles and novel features disclosed herein.

The invention claimed is:

1. A magnetic resonance imaging (MRI) system for selectively showing tractography in areas containing free water, comprising:
    a display;
    at least one processor; and
    a memory storing instructions that, when executed by the at least one processor, cause the MRI system to perform:
    applying a free water correction algorithm to the MRI image and assigning degree of free water values to each tract and/or fragment of tract geometry in the MRI image;
    displaying a graphical user interface on the display having a first area for displaying the MRI image, and a second area with user interface elements for controlling aspects of the MRI image displayed in the first area;
    displaying a free water correction slider interface in the second area for indicating a threshold of free water, in response to which the MRI system compares the degree of free water values to the threshold indicated by the slider interface and refreshing the MRI image so that only those tracts and/or fragments of tract geometry having degree of free water values less than or equal to the threshold are displayed, while others are hidden,
    wherein the free water correction slider interface includes a track showing a range of user selectable free water thresholds from 0% to 100%, a position indicator that can be moved along the track, a value label over the position indicator to display the selectable free water threshold value as a numeral, and the free water correction slider interface further includes icons at opposite ends of the track to provide a visual representation of ranges of threshold values from 0% to 100%.

2. A method for selectively showing tractography in areas containing free water, comprising: generating a magnetic resonance imaging (MRI) image;
    applying a free water correction algorithm to the MRI image and assigning degree of free water values to each tract and/or fragment of tract geometry in the MRI image;
    generating a graphical user interface on a display having a first area for displaying the MRI image, and a second area with user interface elements for controlling aspects of the MRI image displayed in the first area;
    generating a free water correction slider interface in the second area for indicating a threshold of free water;
    comparing the degree of free water values to the threshold indicated by the slider interface; and
    refreshing the MRI image so that only those tracts and/or fragments of tract geometry having degree of free water values less than or equal to the threshold are displayed, while others are hidden,
    wherein the free water correction slider interface includes a track showing a range of user selectable free water thresholds from 0% to 100%, a position indicator that can be moved along the track, a value label over the position indicator to display the selectable free water threshold value as a numeral, and the free water correction slider interface further includes icons at opposite ends of the track to provide a visual representation of ranges of threshold values from 0% to 100%.

* * * * *